(12) United States Patent
Sasnett et al.

(10) Patent No.: US 6,287,299 B1
(45) Date of Patent: Sep. 11, 2001

(54) FLUENCE MONITORING APPARATUS FOR PULSED-LASER CORNEAL RESHAPING SYSTEM

(75) Inventors: Michael W. Sasnett, Los Altos; R. Russel Austin, Novato, both of CA (US)

(73) Assignee: Coherent, Inc., Santa Clara, CA (US)

( * ) Notice: Subject to any disclaimer, the term of this patent is extended or adjusted under 35 U.S.C. 154(b) by 0 days.

(21) Appl. No.: 09/315,894

(22) Filed: May 21, 1999

Related U.S. Application Data (62) Division of application No. 08/971,318, filed on Nov. 17, 1997, now Pat. No. 5,928,221.

(51) Int. Cl.⁷ .................................................. A61F 18/00
(52) U.S. Cl. ................................. 606/12; 606/10; 606/5
(58) Field of Search .............................. 606/4–6, 9, 10, 606/11, 13, 17, 18

(56) References Cited

U.S. PATENT DOCUMENTS

| | | | |
|---|---|---|---|
| 4,911,711 | 3/1990 | Telfair et al. | 606/5 |
| 5,520,679 | 5/1996 | Lin | 606/5 |
| 5,599,340 | 2/1997 | Simon et al. | 606/4 |
| 5,624,437 | 4/1997 | Freeman et al. | 606/12 |
| 5,720,894 | 2/1998 | Neev et al. | 216/65 |
| 5,782,822 | 7/1998 | Telfair et al. | 606/5 |

*Primary Examiner*—David M. Shay
(74) *Attorney, Agent, or Firm*—Stallman & Pollock LLP (57) ABSTRACT

Fluence monitoring apparatus is disclosed for a system for modifying curvature of the cornea of an eye by selective laser photoablation of corneal tissue by delivery of pulses of laser radiation to the cornea in an overlapping pattern. The system includes a scanner for directing the pulses to form the overlapping pattern, the movement of which is modified by an eye-tracker. A beamsplitter is located between the scanner and the cornea for directing a fraction of each of the pulses to a fixed monitor plate, which emits fluorescent light on being irradiated by each pulse-fraction. A video camera 100 images the monitor plate. Processing circuitry periodically records the image which includes images of pulse-fractions delivered during the period between recordings. These recordings are electronically integrated and processed to form a composite image representative of spatial distribution of laser fluence on the cornea.

4 Claims, 8 Drawing Sheets

FLUENCE MONITORING APPARATUS FOR PULSED-LASER CORNEAL RESHAPING SYSTEM

REFERENCE TO PRIOR U.S. APPLICATIONS

This is a divisional of application Ser. No. 08/971,318, filed Nov. 17, 1997, now U.S. Pat. No. 5, 928,221.

TECHNICAL FIELD OF THE INVENTION

The present invention relates in general to a method for laser-beam fluence measurement in laser treatment of biological tissue procedures. The present invention relates in particular to apparatus for measuring spatial distribution of laser-beam energy in a laser ophthalmic surgical procedure wherein corneal curvature is modified by selective photoablation of corneal tissue by means of successive laser pulses incident on the cornea in an overlapping pattern.

DISCUSSION OF BACKGROUND ART

In laser surgical treatment procedures an area to be treated is often irradiated with laser energy in a series of overlapping pulses rather than with a single pulse covering the entire area. This method can provide more accurate and safer dosage, and is also effective when dosage must vary across the treatment area.

In laser ophthalmic surgery systems, in particular those in which a uv-laser beam is used for corneal curvature modification by laser photoablation of corneal tissue, it can be useful to monitor the laser beam. This can be done, for example, for controlling the laser beam or for estimating the extent of photoablation. In early laser ophthalmic surgery systems, treatment pulses were typically centered in the area being treated, variable dosage being obtained by systematically changing the area irradiated by overlapping pulses. Monitoring of laser energy delivered to the target area was restricted to a measurement of the fluence profile of the treatment laser beam.

By way of example, U.S. Pat. No. 4,911,711, issued Mar. 27, 1990, to Telfair et al., discloses a uv-laser photoablation system which includes such a laser beam monitoring device. An operative uv-laser beam of the system is expanded to a relatively large area which terminates with a fixed cornea impingement axis, aligned with the axis of a patient's eye. The intensity profile of the laser beam is one system parameter which is selected to effect a particular corneal curvature modification.

The laser beam monitoring device includes a video camera sensitive to UV radiation. The video camera is coupled with suitable electronic circuitry to monitor the fluence profile of the operative uv-laser beam during a corneal curvature modifying operation. This is done to monitor changes in the laser beam fluence profile. The monitored laser beam fluence profile is used to control optical arrangements for further shaping that profile to ensure that the further-shaped profile stays stable during the operation.

More recent uv-photoablation systems for corneal curvature modification employ pulsed uv-lasers and arrangements for delivering a sequence or succession thousands of relatively low energy pulses in an overlapping pattern over an area of the cornea to be modified. The area of ablation spots created by these pulses is a relatively small fraction of the total area to be treated, for example, five percent or less, and is not centered therein. The extent to which corneal tissue is photoablated at a given site is determined by the total energy that impinges on that site. Examples of such systems are disclosed in U.S. Pat. No. 5,599,340, issued Feb. 4, 1997 to Simon et al. and U.S. Pat. No. 5,520,679, issued May 28, 1996, to Lin.

These types of system present a unique problem in monitoring laser-radiation fluence deposition, as it is the distribution of cumulative energy, on the cornea that determines curvature modification, rather than the energy distribution in the ablating laser beam. In such systems, in fact, the overlapping-pulse pattern compensates for non-uniformity and temporal variations in the energy distribution of the laser beam. An additional problem is presented if the monitored energy distribution is to be relied on as an accurate estimation of a photoablation profile. This is because photoablation is not linearly dependent on absorbed energy. In order to achieve a reasonably accurate estimate of a photoablation profile from an energy distribution measurement, this non-linearity must be taken into account.

It is believed that these problems of cumulative laser-beam energy distribution monitoring for estimation of photoablation have not been addressed in the prior art. A more detailed discussion of these problems, and effective solutions therefor, are presented in the description of the present invention set forth below.

SUMMARY OF THE INVENTION

The present invention is directed to providing laser-beam fluence monitoring apparatus for a system for irradiating a treatment area. The system includes means for generating a succession of pulses of laser radiation, and principal scanning means for directing the laser-radiation pulses toward the treatment-area in an overlapping pattern corresponding to a desired treatment effect. In one aspect, he fluence monitoring apparatus comprises an optical beam-dividing element located between the scanning means and the treatment-area, the beam dividing element arranged to direct a fraction of each of the successive laser-radiation pulses along a first optical path to a monitor plate.

The monitor plate is a plate of a material which emits fluorescent light in response to irradiation by the laser radiation, in an amount proportional to the amount of the laser radiation. A video camera provides an electronic image of the monitor plate. Image processing electronics are arranged for periodically capturing the electronic image and processing the periodically-captured images to provide an integrated electronic image representative of the total laser-beam fluence distribution on the treatment area.

A fluence monitor in accordance with the present invention may be used simply to measure an accumulated radiation dose. Alternatively or additionally the apparatus may be arranged to represent an anticipated effect of that accumulated dose taking into account characteristic response to the laser radiation of material being irradiated.

In one preferred embodiment, fluence monitoring apparatus in accordance with the present invention is used in a system for modifying curvature of a cornea by selective laser photoablation of corneal tissue. The system includes means for generating a succession of pulses of laser-radiation, and principal scanning means for directing the laser-radiation pulses toward the cornea in an overlapping pattern corresponding to a desired pattern of photoablation.

The beam dividing element is arranged to direct a fraction of each of the successive laser-radiation pulses along a first optical path to a monitor plate, and transmit the remaining portion of each of the successive laser pulses along a second optical path to the cornea. The periodically-recorded images provide an integrated electronic image representative of the distribution of laser-beam fluence (total dose of radiation) on the cornea.

In another preferred embodiment of laser-beam fluence monitoring apparatus in accordance with the present invention, the image processor means are programmed to correct integrated, periodically-recorded images for a photoablation threshold energy, below which photoablation is assumed not to occur.

In yet another preferred embodiment of the present invention, wherein the system includes an eye tracker device cooperative with the principle scanning means for compensating for eye-movement during a treatment period, the image processor means are cooperative with the eye tracking device to correct integrated, periodically-recorded images for the action of the scanning means in compensating for eye-movement. In still another preferred embodiment of the present invention, also for use in a system including such an eye-tracker device, a second scanning means is located in the first optical path between the beam-dividing element and the monitor plate. The second scanning means is cooperative with the eye-tracking device for negating eye-movement-correcting actions of the principal scanning means.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DETAILED DESCRIPTION OF THE INVENTION

Before presenting a description of preferred embodiments of laser-beam fluence monitoring apparatus in accordance with the present invention, relevant aspects of a laser photoablation procedure of the type to which the apparatus is directed are described with reference to FIGS. 1A and 1B. In this type of procedure, corneal curvature is modified by selectively removing, by photoablation, corneal tissue in an amount sufficient to achieve the modification. The procedure is described in only sufficient detail to allow one skilled in the art to which the present invention pertains to understand principles of the invention. For those requiring further details, a description of apparatus and a method for carrying out such a procedure is given in U.S. Pat. No. 5,599,340.

Figure 1A:
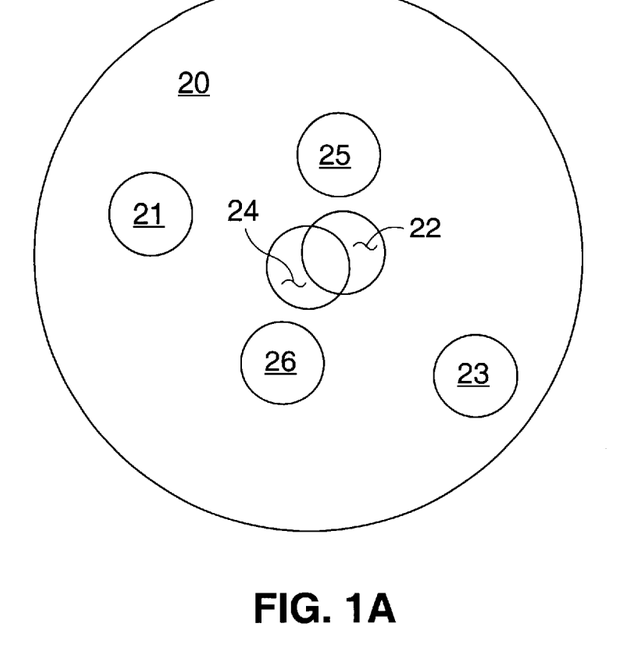
FIGS. 1A and 1B schematically illustrate a method of corneal photoablation by means of a predetermined overlapping pattern of laser pulses.
Figure 1B:
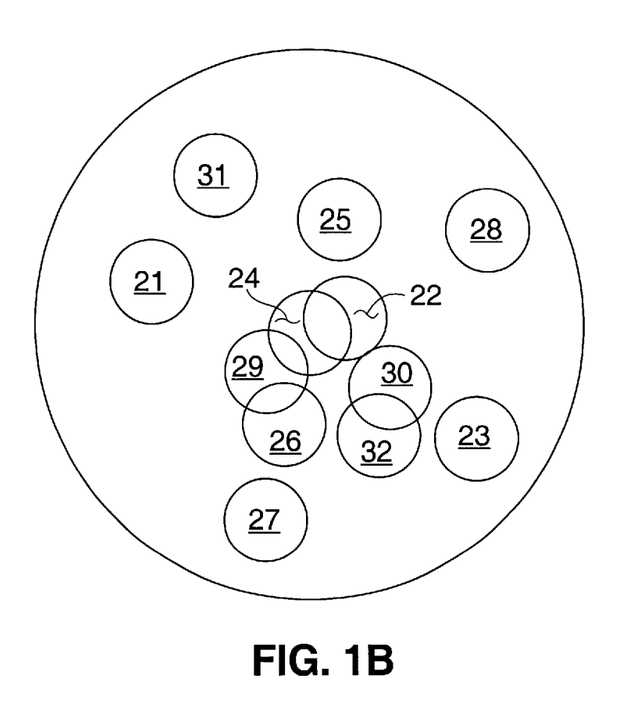

Continuing now with reference to FIGS. 1A and 1B, removal of corneal tissue is effected by irradiating an area 20 of the cornea to be corrected or treated with laser radiation pulses. The pulses are delivered by a laser beam which has a significantly smaller area 22 than the area of the cornea to be corrected or treated, for example, less than 0.05 the treatment area. Preferred beam (pulse diameter) is between about 0.2 and 2.0 millimeters (mm), a beam diameter of about 1.0 mm being particularly preferred. A predetermined overlapping pattern of pulses is delivered to the area, over a treatment period, on a pulse-by-pulse basis. Overlapping pulses serves to compensate for irregularities of spatial energy distribution in the pulse beam area, overlapping pulses also allows removal of corneal tissue to a depth greater than would be comfortably and controllably achievable with a single pulse. Pulse energy is typically kept at a level which will remove tissue only in the instant area irradiated without significantly heating surrounding areas. Further, overlapping pulses can provide a smooth corneal surface after treatment.

For any given corneal curvature modification, a specific pattern of overlapping pulses is first developed and programmed into a system for delivering the pulses. The system is arranged to deliver a succession of pulses, typically, temporally equispaced. Pulse repetition frequencies (rates) may be between about ten and several hundred Hertz (Hz). By way of example, at a preferred pulse rate of 200 Hz, a treatment period may be about twenty to sixty seconds in duration.

Preferably, but not necessarily, such a system is arranged to deliver pulses to different spaced-apart positions on a cornea to be treated. Spacing sequentially delivered pulses apart avoids heat accumulation in a particular area of the cornea. Site selection for successive pulses may be random or according to a particular algorithm. In FIG. 1A, six sequentially delivered pulses 21–26 are depicted in a treatment area 20. In FIG. 1B, six additional pulses 27–32 are depicted in the treatment area. Treatment is continued until the entire treatment area has been irradiated with the specific pattern of pulses.

The above-described procedure is but one procedure to which fluence monitoring apparatus in accordance with the present invention. The apparatus is applicable, for example, in a procedure wherein pulse cross-sections are not circular, but are in the form of a regular polygon, such as a hexagon or square. This allows "tiling" of pulses, with overlapping pulses exactly, rather than partially, overlapping to effect selective ablation.

Figure 2:
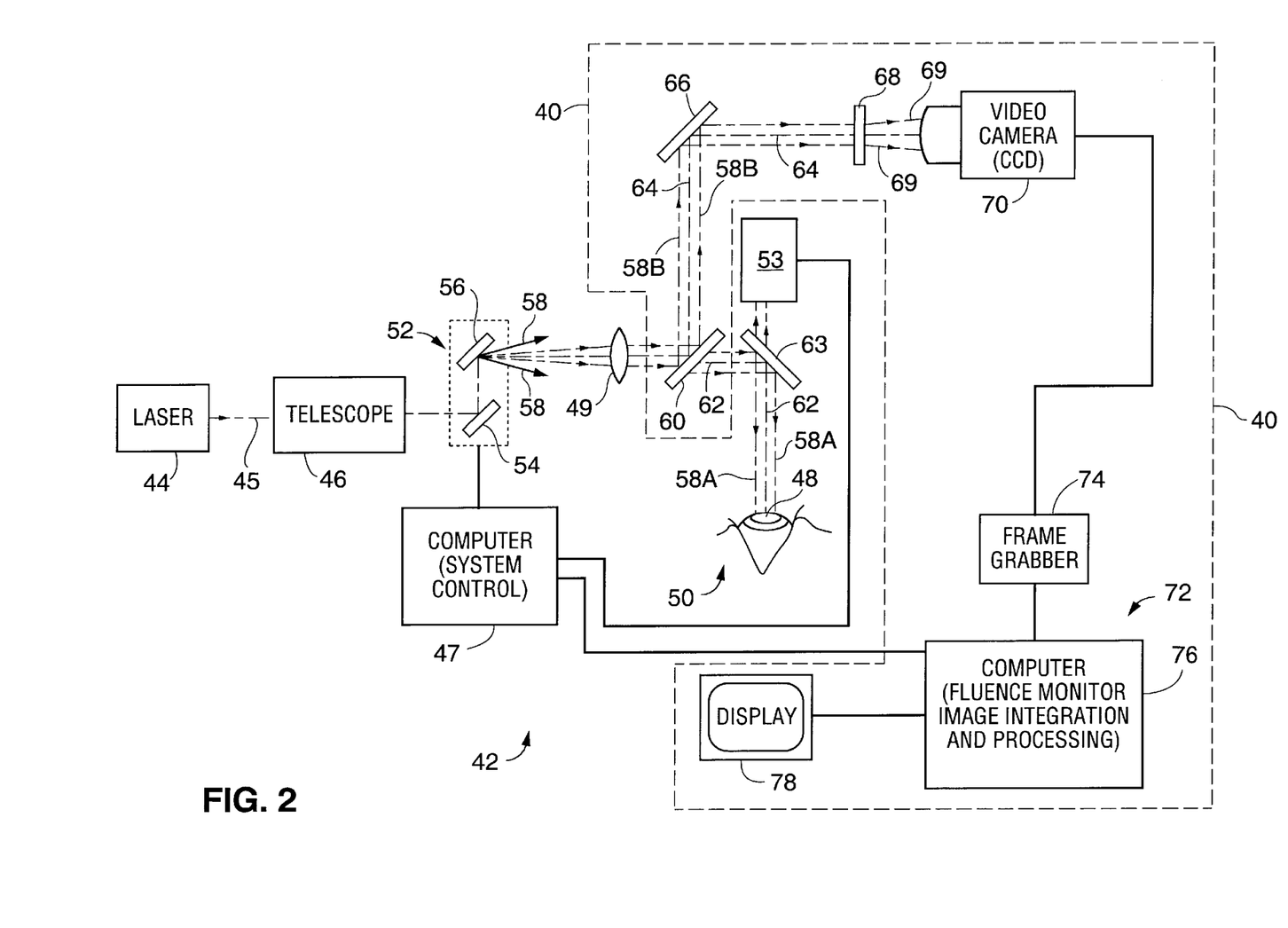
FIG. 2 schematically illustrates a preferred embodiment of fluence monitoring apparatus in accordance with the present invention including a beam-dividing element for sampling a scanned beam, and a video camera arrangement for providing an electronic image of the sampled, scanned beam.

Referring now to FIG. 2, a preferred embodiment of laser-beam fluence monitoring apparatus 40 in accordance with the present invention is depicted. The apparatus is incorporated in a laser surgical system 42.

For clarity, only those components of system 42, in addition to apparatus 40, which are relevant to understanding principles of the present invention are shown, as follows.

Laser 44, is for generating a sequence of laser pulses (illustrated simply by beam 45), typically at an ultraviolet wavelength less than about 230 nanometers (nm), for example 193 nm for an argon fluoride (ArF) excimer laser, or 213 nm for a frequency quintupled Nd:YAG solid state laser. A telescope 46 and collimating lens 49 are provided for imaging the pulses on the cornea 48 of an eye 50 to be treated. A two axis (XY) scanner 52, for directing individual pulses to selected locations on the cornea, includes scanning mirrors 54 and 56 rotatable in mutually orthogonal directions. Individual pulses may be directed or "deflected" at any angle within a cone of directions represented by arrows 58 which, for simplicity, is referred to hereinafter as a "scanned-beam". A system-control computer 47 drives scanner 52.

System 42 includes an eye tracking device (eye-tracker) 53. Eye tracker 53 includes a fixation device (not shown) for preventing gross eye movement during treatment. Eye-tracker 53 tracks relatively small rapid movements of cornea 48 and transmits these to computer 47. Computer 47 controls scanner 52 to take the movement into account in directing pulses to a desired location on cornea 48. Several types of eye tracker are extensively described in the prior art. Accordingly, description of eye-tracker 53 is limited herein to functional aspects thereof. The impact of eye-tracker 53 on fluence monitoring apparatus 40, and arrangements for compensating for actions of the eye-tracker in monitoring laser-beam fluence are discussed in detail further hereinbelow.

Continuing now with a description of laser-beam fluence monitoring apparatus 40, a pick-off or beam-dividing mirror 60 transmits a major portion 58A of scanned beam 58, preferably greater than about 90% along an optical path 62 toward cornea 48. Scanned beam portion 58A is directed by a fold mirror 63 to cornea 48. Fold-mirror 63 is made reflective for the wavelength of the ultraviolet radiation pulses, and transmissive of IR wavelengths (about 880 nm) by which eye-tracker 53 functions.

Pick-off mirror 60 reflects a minor portion 58B of scanned beam 58, i.e., that fraction not transmitted, scattered or absorbed by the mirror, along an optical path 64 via a fold-mirror 66 to a monitor plate 68. It is emphasized here that what is meant by major and minor fractions of scanned beam 58 is major and minor fractions of sequential pulses making up scanned beam 58. In one preferred example pick-off mirror 60 is simply a transparent fused-silica substrate, antireflection coated for the laser wavelength on only one surface thereof h. Fresnel reflection at the uncoated surface reflects about 5% of light incident thereon along path 64.

Monitor plate 68 is formed from a transparent material which emits fluorescent light on being irradiated by light having the wavelength of laser radiation pulses in scanned beam 58. For pulses having a wavelength of 213 nm a preferred material is lightly-doped sapphire (Ti:sapphire). Such Ti:sapphire plates are commercially available from Crystal Systems Inc. of Salem, Mass.

Fluorescent light 69 is emitted by plate 68 in response to receiving a fraction of a pulse in scanned-beam portion 58B. The light is emitted at the location on the plate at which the pulse-fraction is incident and is emitted in an amount proportional to the amount (energy) of light in the pulse. For Ti:sapphire material, at least, this proportion is about linear. When, as depicted in FIG. 2, there are no optical elements having refractive power in optical paths 62 and 64, and when cornea 48 and monitor plate 68 are optically-equidistant from pick-off mirror 60, the pattern of pulses on cornea 48 will be reproduced, with a uniformly reduced energy distribution, on monitor plate 68. The energy distribution of the reproduced pulse-pattern on the monitor plate will in turn be represented by a corresponding pattern of sequential ultraviolet light emissions.

Monitor plate 68 is imaged by a video camera 70, preferably a charge-coupled-diode (CCD) camera. Video camera 70 will "see" the fluorescent emission generated by each incident pulse, as it occurs. As the generation of ultraviolet light by an incident pulse is a transient event, video camera 70 must be provided with an arrangement to capture these events and interpret them in a manner which will provide a representation of spatial distribution of energy or fluence distribution over a treatment (corneal curvature modification) period.

Figure 3:
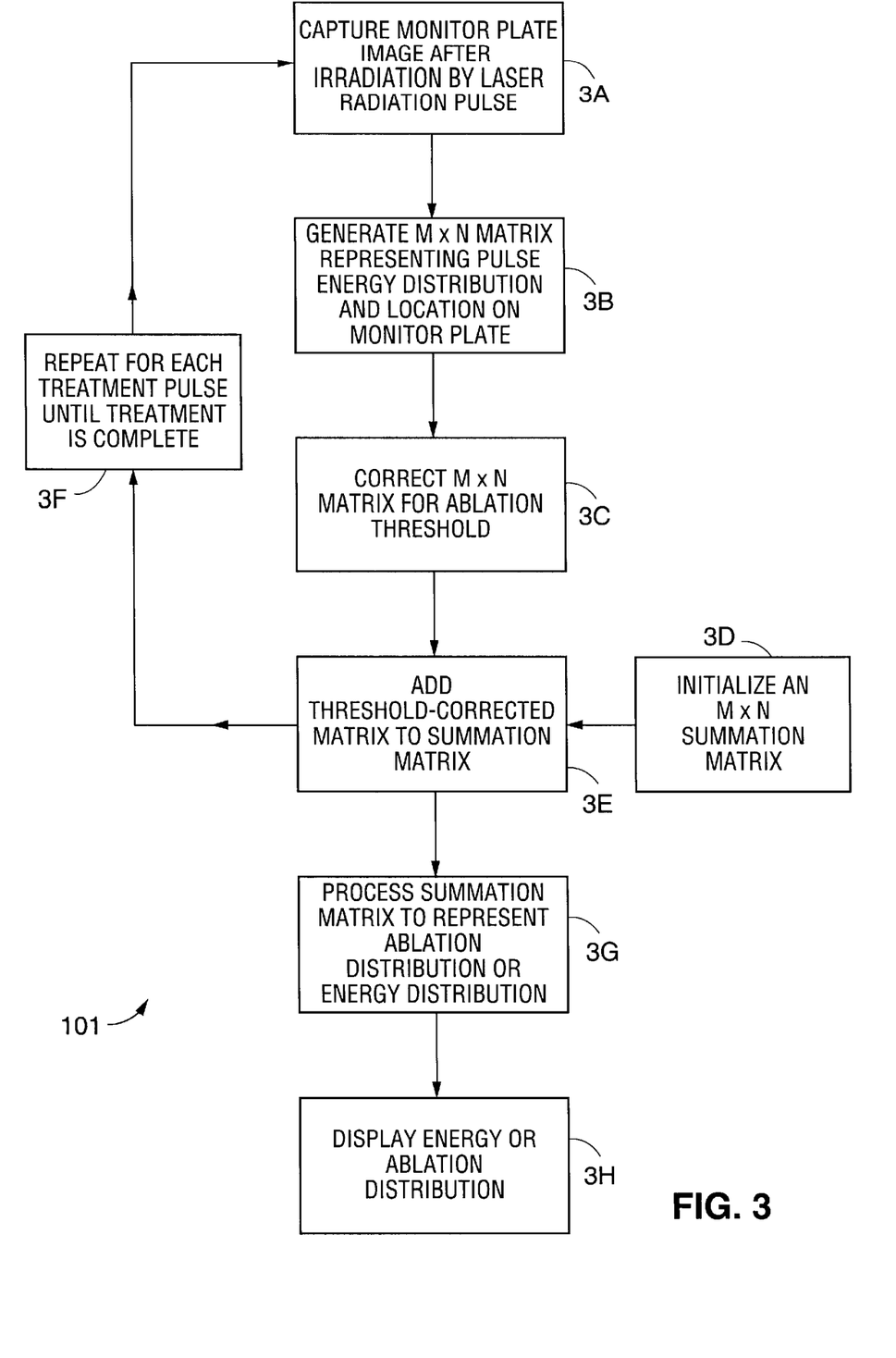
FIG. 3 is a flow chart schematically illustrating a method of electronic image capture and processing in the fluence monitoring apparatus of FIG. 2.

Continuing now with reference to FIG. 2 and additionally to the flow-chart of FIG. 3, in one particularly preferred method 101 of capturing and interpreting these events, image processing circuitry 72 is provided with a frame-grabber 74 for capturing images, and a computer 76 for integrating and processing captured images.

It should be noted here that while computers 47 and 76 are shown as separate entities in FIG. 2, this should not be considered as limiting. Those skilled in the system control art will recognize many other computer or microprocessor arrangement which can carry out control and processing functions of system 42 and laser-beam fluence monitoring apparatus 40 discussed herein.

In one preferred arrangement, frame grabber 74 is synchronized to sequentially capture the image seen by video camera 70 at the rate at which laser pulses in scanned-beam portion 58B are incident on monitor plate 68, i.e., an image is captured after each pulse (FIG. 3 box 3A). The captured image is stored as a rectangular matrix or array of M×N pixels of a selected bit-value (FIG. 3 box 3B). Eight bits per pixel provide a magnitude resolution of 256 levels which is adequate for most applications of the present invention. The M×N pixels may correspond to the same number and arrangement of diodes in a CCD focal plane array. The M×N pixels may also be less than the number and arrangement of diodes in the CCD focal plane array, with more than one diode contributing to a pixel. A captured image will consist of only one fluorescent-light pulse (generated by a pulse portion in scanned-beam 58B) which is defined by a plurality of adjacent pixels of the M×N array.

Figure 4:
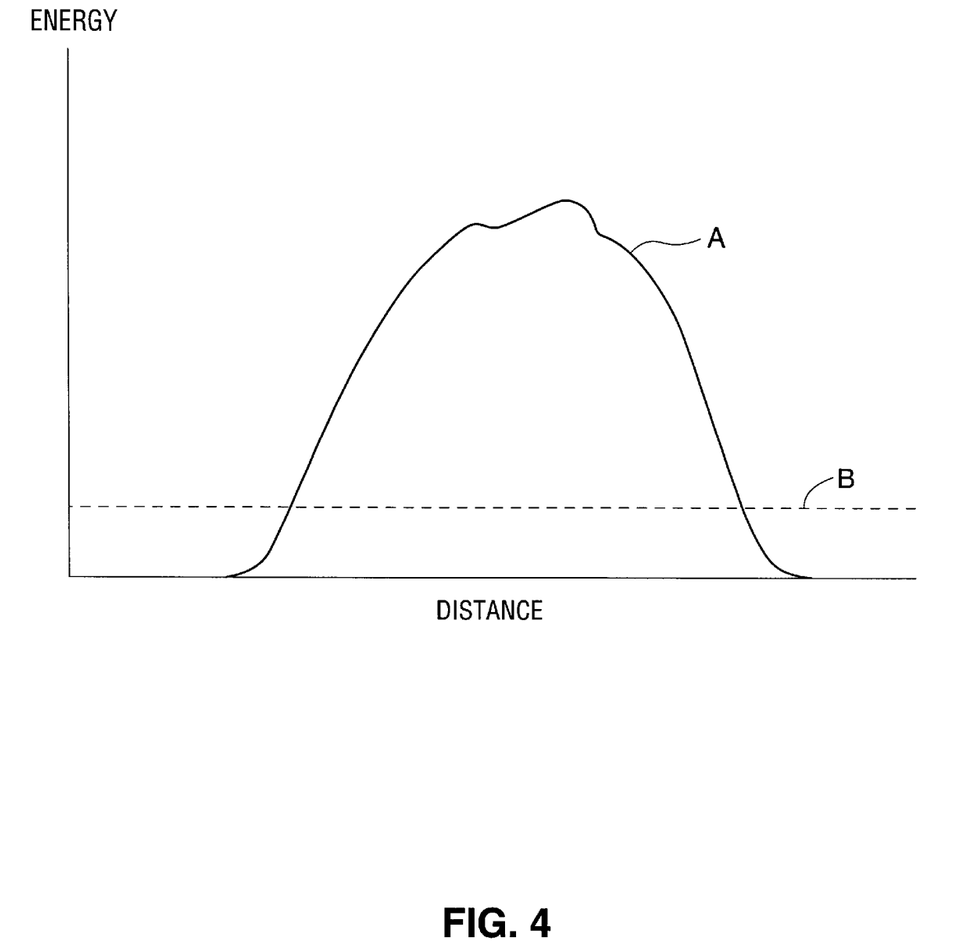
FIG. 4 is a graph schematically illustrating an exemplary energy distribution profile in a laser-radiation pulse of the apparatus of FIG. 2, and an exemplary threshold value of pulse energy which must be exceeded to cause photoablation of corneal tissue.

In a procedure such as referenced in FIGS. 1A and B, the pulse-defining pixels will cover a generally circular area, the plurality of pixels allowing the distribution of energy across the pulse-irradiated area of the monitor plate to be defined. This energy distribution represents, to a first level of approximation, photoablation which will be caused by a corresponding pulse-portion incident on cornea 48. This first level of approximation, however, does not take into account that photoablation typically only occurs above a certain threshold energy level per pulse. This is illustrated in FIG. 4, wherein curve A represents a hypothetical energy distribution across a pulse and curve B represents the threshold energy for photoablation.

To correct for photoablation-threshold energy, pulse energy values are reduced by the photoablation-threshold value, any resulting negative values, of course, being set to zero, to form a threshold-corrected matrix. (FIG. 3, step 3C). An M×N summation or integration matrix is initialized to zero, and the corrected matrix is added to the summation matrix (FIG. 3, steps 3D and 3E). Steps 3A–C and step 3E of FIG. 3 are continued (step 3F) while treatment continues. The summation matrix may be processed at intervals of one or more pulses, or after treatment is complete, to represent distribution of integrated energy (laser-beam fluence) deposited on, or accumulated ablation of, cornea 48 (FIG. 3, step 3G). Accordingly, accumulated ablation or laser-beam fluence distribution may be displayed (FIG. 3, step 3H), progressively or finally, on display 78 (see FIG. 2). The display may include, for example, a "map" of grey-scale or color values representing different laser-beam fluence values or ablation depths. Photoablation-threshold values and relationships between energy per pulse and photoablation, useful for representing monitored laser-beam fluence as photoablation, may be determined experimentally, for example, by ablation trials using polymers, gelatin, porcine corneal tissue, or the like.

The above described method of image capture and processing is preferred because it provides for a relatively simple means of providing a relatively accurate, ablation-threshold-corrected approximation of accumulated ablation on cornea 48. Depending on the performance of available CCD camera equipment and processing electronics, however, this method may not be suitable for laser-radiation pulse rates above the 30 Hz or 60 Hz capture rates typical of CCD video camera equipment.

Figure 5:
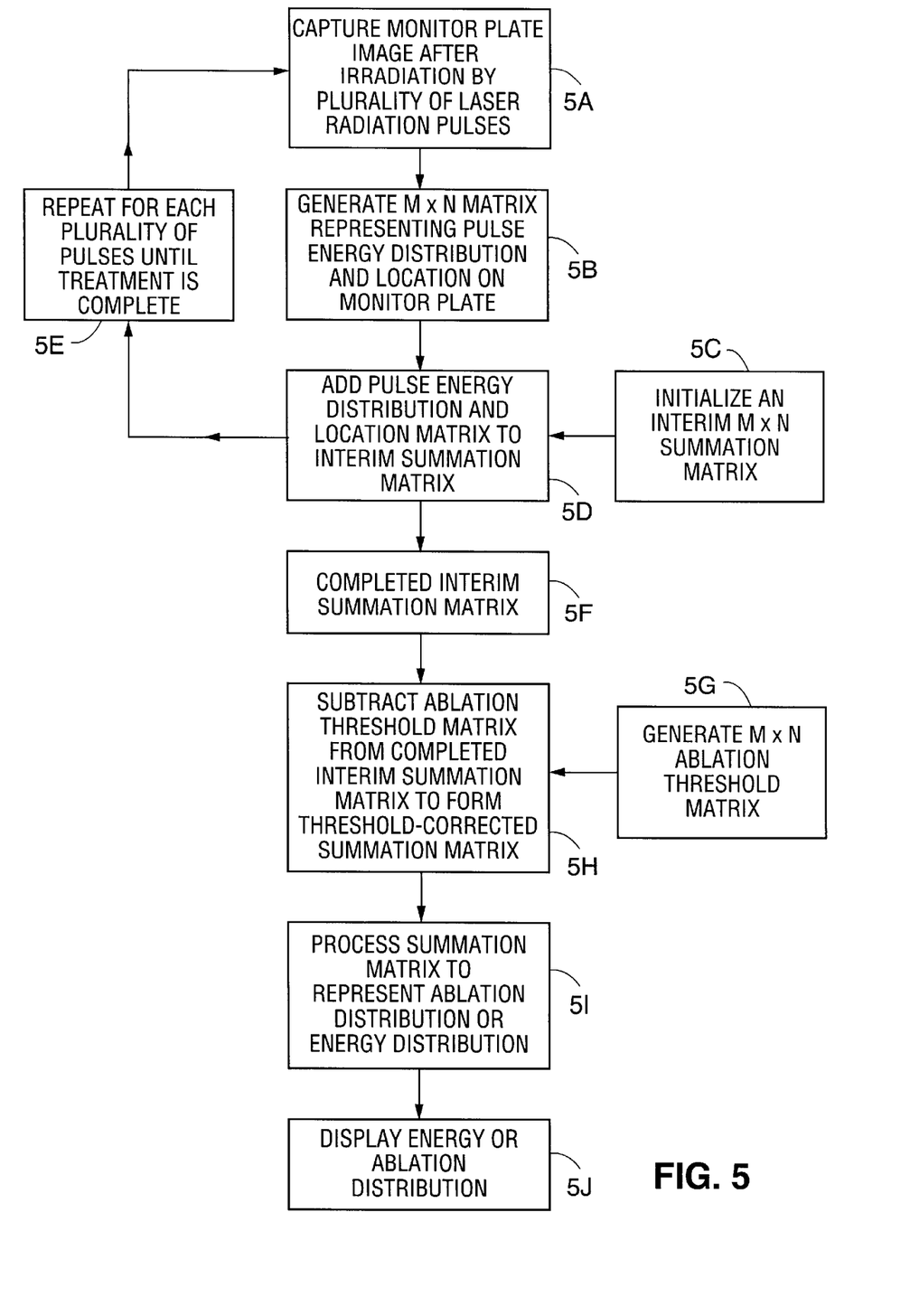
FIG. 5 is a flow chart schematically illustrating another image capture and processing method in the laser-beam fluence monitoring apparatus of FIG. 2.

In scanning laser-ablation systems, lasers emitting pulses at 200 Hz or even higher pulse rates are preferred. Described below with reference to FIG. 5 is an alternate method 102 of image capture and processing which is suitable for a system wherein pulses are delivered at about five to ten times the rate at which an image of monitor plate 48 is captured and processed. The method assumes that sufficient pulses are delivered during a image-capture interval, and that at least two of the delivered pulses will overlap. The method is effective even when the laser-pulse rate is not an exact multiple of the image capture rate.

At one image capture interval after laser radiation is initiated, an image of monitor plate 68 is captured (step 5A). During this time interval, a plurality of laser-radiation pulses will have irradiated the monitor plate. Even though these pulses have arrived sequentially at the monitor plate, the image will include the fluorescent light generated by all of the pulses. Overlapping pulses will be integrated by corresponding diodes in the CCD focal plane of the video camera. From the captured image, an M×N matrix representing laser-radiation pulse-energy distribution (here referring to energy distribution in a pulse and distribution of pulse locations on the plate) on monitor plate 68 is generated (step 5B). An M×N summation matrix is initialized to zero and the pulse-energy-distribution matrix is added to this (steps 5C and 5D). Steps 5A, 5B, and 5B are repeated until the treatment period is complete (step 5E). At this stage, the summation matrix may be defined as the final summation matrix (step 5F).

An M×N threshold-correction matrix is generated (step 5G). This may be computed, for example, by summing (integrating) as many M×N matrices as there are pulses delivered during the treatment period, each of these including a threshold representation of a particular pulse in the final pulse pattern, at the location of that particular pulse. The threshold correction matrix is then subtracted from the final summation matrix and the resulting matrix may be processed and displayed to represent laser-beam fluence or ablation distribution (steps 5I and 5J).

A disadvantage of the image capture and processing method of FIG. 5 is that a threshold-corrected representation of accumulated ablation may only be observed after the treatment period is complete. A description of yet another method 103 of multiple-pulse image capture and processing, which allows display of a progressive threshold-corrected estimate of accumulated ablation is presented below with reference to FIG. 6.

Figure 6:
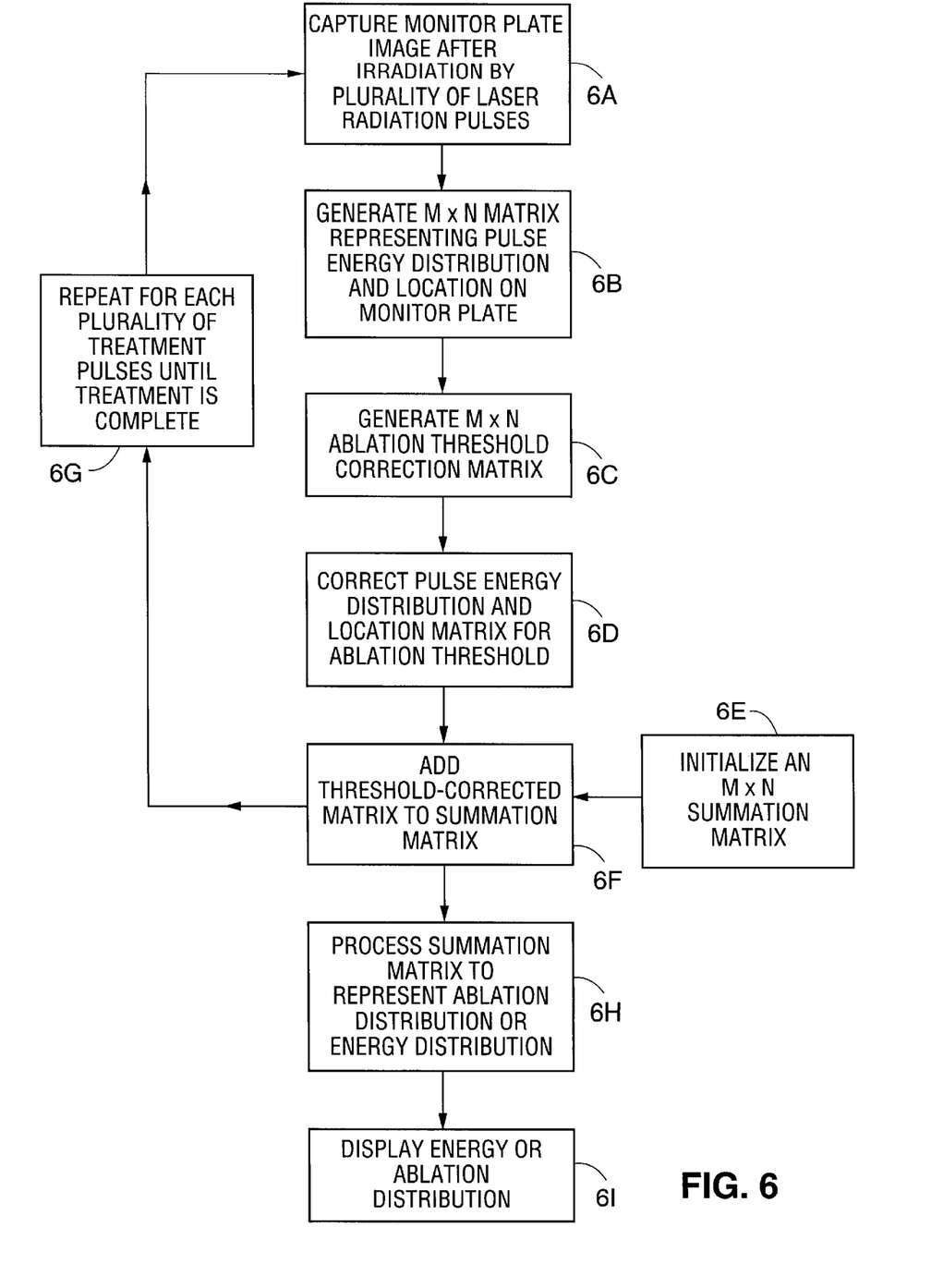
FIG. 6 is a flow chart schematically illustrating another image capture and processing method in the laser-beam fluence monitoring apparatus of FIG. 2.

At one image capture interval (initially, after laser-pulse irradiation begins), an image of the monitor plate 68 is captured (step 6A). During this interval, a plurality of pulses will have irradiated the monitor plate, with results as described above for method 102. from the captured image, an M×N matrix representing pulse-energy distribution on monitor-plate 68 is generated (step 6B). An M×N threshold-correction matrix is generated which includes threshold-level representations corresponding in number and location to the number of pulses during the interval.

The threshold-correction matrix may be generated in a number of ways, depending on the manner in which the pulses are delivered. By way of example, if the laser-pulse delivery rate is an exact multiple of the frame capture rate, and the pulse pattern is delivered in accordance with a predetermined non-random delivery sequence, then a sequence of threshold representations, corresponding to the same sequence of pulses can be integrated into the threshold-correction matrix. Further by way of example, if the laser-pulse delivery rate is not an exact multiple of the frame capture rate, and the pulse pattern is delivered in accordance with a random or partially-random sequence, computer 72 could be arranged to receive from system control computer 47 signals which indicate where a pulse is being delivered and integrate a threshold value into the threshold correction matrix at that location. From these examples, those skilled in the art to which the present invention pertains may devise other threshold correction methods without departing from the spirit and scope of the present invention.

Continuing now with reference to FIG. 6, after the threshold correction matrix has been generated, it is used to correct the pulse-energy distribution matrix and form a corrected pulse-energy distribution matrix (step 6D). An M×N summation matrix is initialized to zero and the corrected pulse-energy distribution matrix is added to this (steps 6C and 6D). Steps 6A–D and 6F are repeated until the treatment period is complete (steps 6G). The summation matrix may be processed and displayed progressively or finally to represent accumulated to represent accumulated ablation (steps 6H and 6I).

It should be noted here that if an application of laser-beam fluence monitoring apparatus 40 does not require the accuracy of a photoablation-threshold correction, steps to correct for photoablation can be omitted from above described capture and processing methods. The manner of doing this will be evident to one skilled in the art to which the invention pertains, and accordingly is not separately described or depicted herein.

Figure 7:
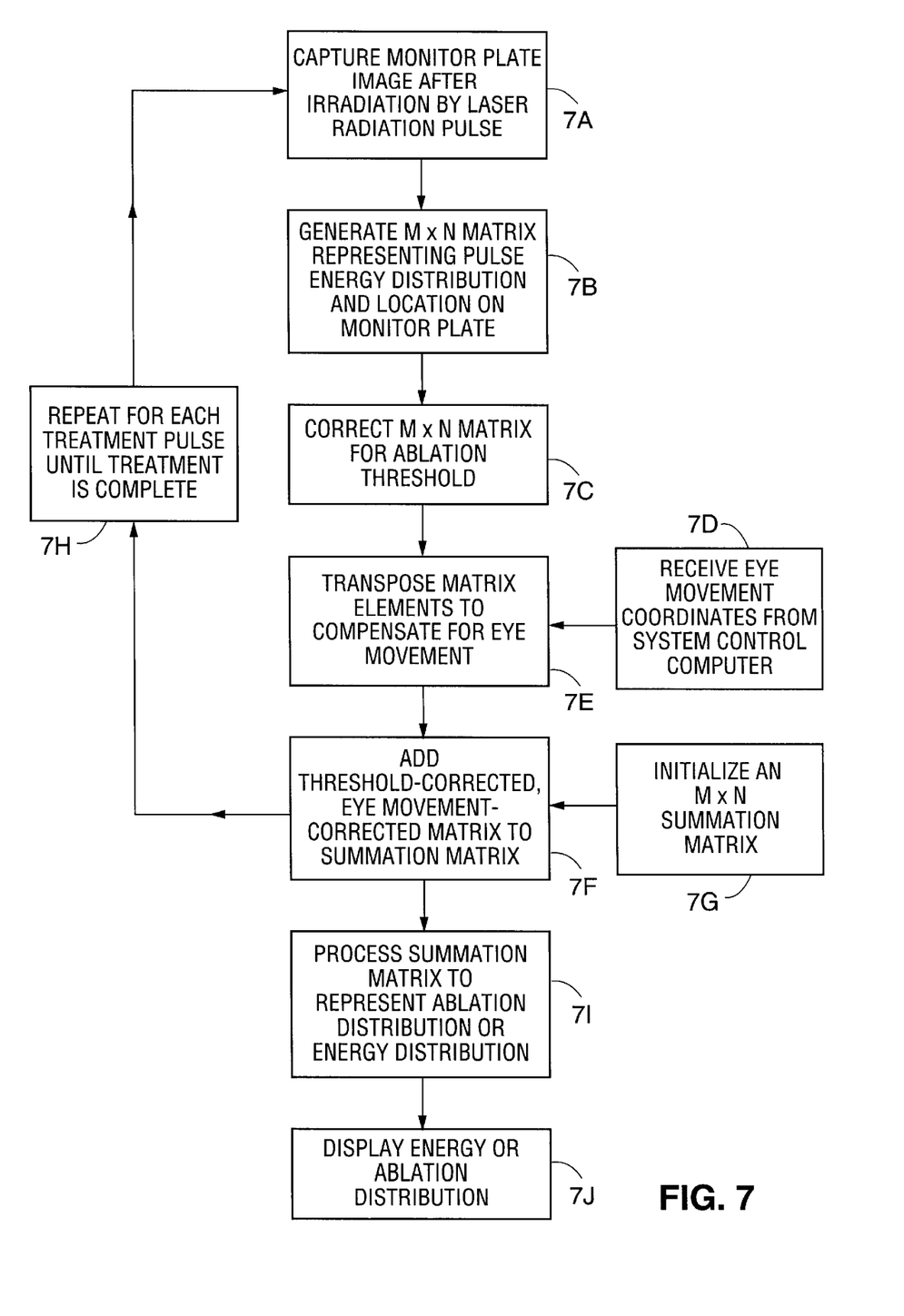
FIG. 7 is a flow chart schematically representing a method of applying compensation for eye-movement correction in the scanned beam of the apparatus of FIG. 2 to the image capture and processing method of FIG. 3.

Continuing now with a description of another aspect of accuracy in laser-beam fluence monitoring apparatus in accordance with the present invention, it is pointed out that apparatus 40, used according to the descriptions presented above, can not present an optimally accurate estimate of photoablation distribution during an actual operation in which eye-tracker 53 is operational. This is because monitor plate 68 remains fixed while cornea 48 is moving. Laser-beam fluence monitoring apparatus 40 as described above can still, of course, be used in an optimally accurate way for calibrating and adjusting system 42 prior to an operation, in effect, for "rehearsing" an operation before cornea 48 is irradiated. It is useful, however, to have an equally accurate estimate of photoablation which occurs during an operation. This can be useful, for example, in evaluating results of an operation by comparing the estimate with corneal topographic measurements made, for example, by well-known interferometric means. Set forth below with reference again to FIG. 2, and additionally to FIG. 7, is one method by which fluence monitoring apparatus 40 can be arranged to compensate for eye-movement during an operation.

Referring first to FIG. 2, system control computer 47 is arranged to deliver eye-movement information received from eye-tracker 53 to computer 76. The eye-movement information is interpreted by computer 76 as integer X-Y coordinates corresponding to elements of an M×N matrix which is used to represent a captured monitor image. Referring now to FIG. 7, one method 104 for applying these coordinates to apply eye-movement correction in image capture and processing method 101 of FIG. 3 is described. Those skilled in the art will recognize from the description set forth below that while eye correction method 104 is described here as a modification of method 101, it may also be applied to methods 102 and 103.

In method 104, an image of monitor plate 68 is captured (step 7A), an M×N matrix representing pulse-energy distribution is generated (step 7B), and the matrix is corrected for ablation threshold step 7C. Steps 7A–C correspond to steps 3A–C of FIG. 3.

Eye movement coordinates received from system control computer 47 (step 7D) are used to transpose elements of the threshold corrected M×N matrix (step 7E). Transposition is such that the image represented by the threshold-corrected, eye-movement-corrected matrix is essentially "displaced" by the amount of the eye movement, thereby negating the effect of eye movement. For example, if eye movement is represented by XY coordinates (p, q), a value at matrix element $E_{(i,j)}$ would be transposed to matrix element $E_{(i-p, j-q)}$.

An initial threshold-corrected, eye-movement-corrected matrix is added to an initialized summation matrix (steps 7F and 7G). Steps 7A–F are repeated (step 7H) until treatment is complete. The summation matrix can be processed progressively or finally to represent laser-beam fluence distribution or ablatio distribution (steps 7I and 7J).

Figure 8:
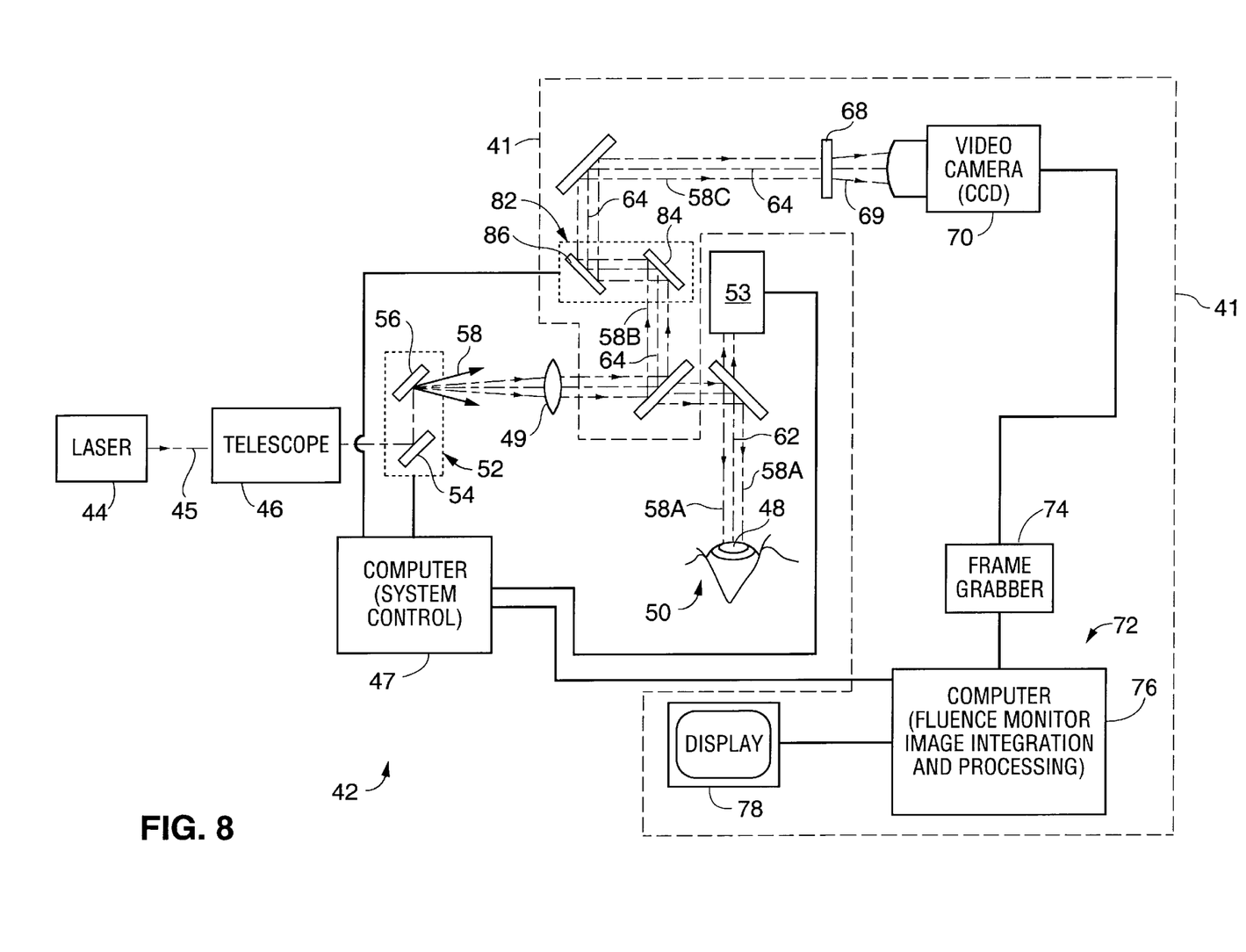
FIG. 8 schematically illustrates a preferred embodiment of fluence monitoring apparatus in accordance with the present invention including a device for negating eye-movement-compensating direction changes in the scanned beam of FIG. 2.

Referring now to FIG. 8, another embodiment 41 of laser-beam fluence monitoring apparatus in accordance with the present invention is described. Apparatus 41 includes all components of apparatus 40 and also includes a scanner 82 located in optical path 64 between pick-off mirror 60 and monitor plate 68. Scanner 82 includes mirrors 84 and 86 for directing pulses in beam 58B in respectively X and Y (mutually orthogonal) axes corresponding to the X and Y axes.

Scanner 82 is controlled by system computer 47 using eye-movement displacement signals received from eye-tracker 53. Control of scanner 82 is arranged such that these eye-movement signals cancel or negate the eye-movement correction which is present in scanned-beam portion 58B. Because of this, pulse-fractions in scanned beam 58C leaving scanner 82 will be incident on monitor plate 68 at a location thereon corresponding to the location of the remainder of the pulse on cornea 48. Image capture and processing in apparatus 41 may be carried out in accordance with any of methods 101–103 described above.

In summary, laser-beam fluence monitoring apparatus in accordance with the present invention is configured for use in a system for effecting corneal curvature modification by means of photoablation of corneal tissue by a sequence of pulses from a uv-laser. The system delivers the pulses to a cornea in an overlapping pattern, the distribution of cumulative laser-beam fluence in the pattern of pulses determines the curvature modification. The inventive laser-beam fluence monitoring apparatus electronically captures fluorescent-light images representative of pulses delivered during a treatment period, and integrates (sums) and processes these electronically-captured images to provide a representation of the distribution of laser-beam fluence on the cornea. Laser beam fluence distribution in turn can be represented as photoablation distribution on the cornea.

Image capture and processing methods include, in addition to image integration, correction of captured or summed images for photoablation threshold, or for eye-movement correction applied by the system in delivering the pulses.

While the present invention has been described in terms of its use in laser corneal curvature modifying apparatus, those skilled in the art to which the present invention pertains will recognize that its use is not limited to such apparatus. The fluence monitoring apparatus of the present invention is useful in any application wherein organic or other tissue or material is modified in some way by treating the tissue or material with a sequence of pulses of laser radiation. Accordingly, the invention such not be construed as being limited to the embodiments described above. Rather the invention is limited by the claims appended hereto.

What is claimed is:

1. Laser-beam fluence monitoring apparatus for a system for modifying curvature of a cornea of an eye by selective laser photoablation Qf corneal tissue, the system including means for generating a sequence of pulses of laser radiation, a scanner for directing the laser-radiation pulses toward the cornea in an overlapping pattern corresponding to a desired cumulative spatial distribution of laser beam fluence on the cornea for providing a desired cumulative spatial distribution of photoablation of the corneal tissue, and an eye-tracker cooperative with the scanner for changing the direction of the laser radiation pulses to compensate for motion of the eye during corneal curvature modification, the fluence monitoring apparatus comprising:

an optical beam-dividing element located between the scanner and the cornea to receive laser-radiation pulses directed by the scanner, the beam dividing element arranged to direct a first fraction of each of the successive laser-radiation pulses received from the scanner along a first optical path to a fixed monitor plate, and transmit a second portion of each of the laser-radiation pulses received from the scanner along a second optical path to the cornea;

said monitor plate being a plate of a material which emits fluorescent light in response to irradiation by the laser radiation, in an amount proportional to the amount of the laser radiation;

a video camera for providing an electronic image of said monitor plate;

image processor means arranged for periodically capturing said electronic image and processing and summing said periodically-captured images to provide an integrated electronic image representative of one of cumulative laser-beam fluence spatial distribution on the cornea above a predetermined photoablation threshold value resulting from the sequence of laser-radiation pulses, and spatial distribution of cumulative ablation depth of corneal tissue resulting from the sequence of laser-radiation pulses; and wherein said processing of said periodically-captured images includes correcting said images to eliminate errors therein due to the eye-motion-compensating pulse-direction changes applied by the scanner.

2. The apparatus of claim 1, further including a display device for visually displaying said integrated electronic image.

3. The apparatus of claim 1, wherein said video camera is a CCD camera.

4. The apparatus of claim 1, wherein each of said captured images is represented by a rectangular matrix of image elements and said correcting of said images includes transposing a said image element from location coordinates (i, j) of said rectangular matrix to location coordinates (i−p, j−q) of said rectangular matrix, where p and q, represent a said eye-motion-compensating pulse-direction change.

* * * * *